US008075611B2

(12) United States Patent
Millwee et al.

(10) Patent No.: US 8,075,611 B2
(45) Date of Patent: Dec. 13, 2011

(54) STENTED PROSTHETIC HEART VALVES (75) Inventors: Billie J. Millwee, Fullerton, CA (US); Mark J. Capps, Mission Viejo, CA (US); Janice L. Shay, Lake Forest, CA (US); Debra A. Taitague, Huntington Beach, CA (US); Mark J. Dolan, Santa Rosa, CA (US); Carol E. Eberhardt, Fullerton, CA (US)

(73) Assignee: Medtronic, Inc., Minneapolis, MN (US)

( * ) Notice: Subject to any disclaimer, the term of this patent is extended or adjusted under 35 U.S.C. 154(b) by 185 days.

(21) Appl. No.: 12/476,702

(22) Filed: Jun. 2, 2009

(65) Prior Publication Data
US 2010/0305685 A1 Dec. 2, 2010

(51) Int. Cl.
*A61F 2/06* (2006.01)
*A61F 2/24* (2006.01)

(52) U.S. Cl. ............ 623/1.24; 623/2.12; 623/2.13; 623/2.14; 623/2.15; 623/2.17; 623/2.19; 623/2.38

(58) Field of Classification Search .......... 623/1.24, 623/1.26, 2.12–2.19
See application file for complete search history.

(56) References Cited

U.S. PATENT DOCUMENTS

| | | | |
|---|---|---|---|
| 5,840,081 A | 11/1998 | Andersen et al. | |
| 5,957,949 A | 9/1999 | Leonhardt et al. | |
| 6,168,614 B1 | 1/2001 | Andersen et al. | |
| 2003/0033003 A1 | 2/2003 | Harrison et al. | |
| 2003/0199963 A1 | 10/2003 | Tower et al. | |
| 2003/0199971 A1 | 10/2003 | Tower et al. | |
| 2004/0030378 A1 | 2/2004 | Khosravi et al. | |
| 2004/0093070 A1 | 5/2004 | Hojeibane et al. | |
| 2006/0206202 A1 | 9/2006 | Bonhoeffer et al. | |
| 2006/0259137 A1 | 11/2006 | Artof et al. | |
| 2007/0288086 A1 | 12/2007 | Kalmann et al. | |
| 2008/0147183 A1* | 6/2008 | Styrc .................. 623/2.12 |

FOREIGN PATENT DOCUMENTS

| | | |
|---|---|---|
| EP | 0 856 300 | 8/2004 |
| WO | 96/21404 | 7/1996 |
| WO | 2007/123658 | 11/2007 |
| WO | 2010/037141 | 4/2010 |

OTHER PUBLICATIONS

Bonhoeffer, et al., "Percutaneous Insertion of the Pulmonary Valve", Journal of the American College of Cardiology 2002; 39: 1664-1669.
Bonhoeffer, P. et al., "Transcatheter Implantation of a Bovine Valve in Pulmonary Position." Circulation, 2000; 102:813-816.
Cribier, A. et al. "Percutaneous Transcatheter Implantation of an Aortic Valve Prosthesis for Calcific Aortic Stenosis." Circulation, 2002; 106:3006-3008.
"Freestyle® Aortic Root Bioprothesis," Medtronic, Inc. 2009 (3 pages).
"Freestyle® Aortic Root Bioprothesis—The Most Physiologic Valve," Brochure, Medtronic, Inc., 2009, (42 pages).

* cited by examiner

*Primary Examiner* — David Isabella
*Assistant Examiner* — Leslie Coburn (57) ABSTRACT

A surgical sutureless valve that is attached to a stent frame for delivery to a location in a patient using percutaneous implantation devices and methods.

10 Claims, 8 Drawing Sheets

STENTED PROSTHETIC HEART VALVES

TECHNICAL FIELD

The present invention relates to prosthetic heart valves. More particularly, it relates to surgical sutureless valves and methods for percutaneously implanting such prosthetic heart valves in combination with a stent structure.

BACKGROUND

Diseased or otherwise deficient heart valves can be repaired or replaced using a variety of different types of heart valve surgeries. Typical heart valve surgeries involve an open-heart surgical procedure that is conducted under general anesthesia, during which the heart is stopped while blood flow is controlled by a heart-lung bypass machine. This type of valve surgery is highly invasive and exposes the patient to a number of potentially serious risks, such as infection, stroke, renal failure, and adverse effects associated with use of the heart-lung machine, for example.

Recently, there has been increasing interest in minimally invasive and percutaneous replacement of cardiac valves. Such surgical techniques involve making a very small opening in the skin of the patient into which a valve assembly is inserted in the body and delivered to the heart via a delivery device similar to a catheter. For certain applications, the technique is preferable to more invasive forms of surgery, such as the open-heart surgical procedure described above. In the context of pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. The replacement valve is mounted on a balloon catheter and delivered percutaneously via the vascular system to the location of the failed pulmonary valve and expanded by the balloon to compress the valve leaflets against the right ventricular outflow tract, anchoring and sealing the replacement valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits.

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprostheses or mechanical heart valve prostheses. In other words, the replacement valves may include a valved vein segment that is mounted in some manner within an expandable stent to make a stented valve. In order to prepare such a valve for percutaneous implantation, the stented valve can be initially provided in an expanded or uncrimped condition, then crimped or compressed around the balloon portion of a catheter until it is as close to the diameter of the catheter as possible.

Other percutaneously-delivered prosthetic heart valves have been suggested that have a generally similar configuration, such as by Bonhoeffer, P. et al., "Transcatheter Implantation of a Bovine Valve in Pulmonary Position." Circulation, 2002; 102:813-816, and by Cribier, A. et al. "Percutaneous Transcatheter Implantation of an Aortic Valve Prosthesis for Calcific Aortic Stenosis." Circulation, 2002; 106:3006-3008, the disclosures of which are incorporated herein by reference. These techniques rely at least partially upon a frictional type of engagement between the expanded support structure and the native tissue to maintain a position of the delivered prosthesis, although the stents can also become at least partially embedded in the surrounding tissue in response to the radial force provided by the stent and balloons that are sometimes used to expand the stent. Thus, with these transcatheter techniques, conventional sewing of the prosthetic heart valve to the patient's native tissue is not necessary. Similarly, in an article by Bonhoeffer, P. et al. titled "Percutaneous Insertion of the Pulmonary Valve." J Am Coll Cardiol, 2002; 39:1664-1669, the disclosure of which is incorporated herein by reference, percutaneous delivery of a biological valve is described. The valve is sutured to an expandable stent within a previously implanted valved or non-valved conduit, or a previously implanted valve. Again, radial expansion of the secondary valve stent is used for placing and maintaining the replacement valve.

Although there have been advances in percutaneous valve replacement techniques and devices, there is a continued desire to provide different designs of cardiac valves that can be implanted in a minimally invasive and/or percutaneous manner.

SUMMARY

Certain surgically implanted prosthetic heart valves, such as the aortic root bioprostheses commercially available under the trade designation "Freestyle" from Medtronic, Inc., of Minneapolis, Minn., have proven to have certain advantages over other bioprostheses used in aortic valve replacement. However, the implantation of these Freestyle types of valves is limited to surgeons who have become specifically skilled in the surgical implantation of homografts. The replacement heart valves of the invention are provided to overcome these limitations and are directed to attachment of a surgical heart valve into a patient without the use of sutures. In this way, the advantages of certain surgical valves can be achieved without the disadvantages of surgical valve implantation procedures. That is, the invention provides a sutureless implantation of a surgical valve, such as an aortic root bioprosthesis, which would typically be implanted into a patient using more traditional surgical techniques. The prosthetic heart valves of the invention include valves that are compressible to a relatively small diameter for percutaneous delivery to the heart of the patient, and then are expandable either via removal of external compressive forces (e.g., self-expanding stents), or through application of an outward radial force (e.g., balloon expandable stents).

The replacement heart valves of the invention include a stent to which a valve structure is attached. The stents of the invention include a wide variety of structures and features that can be used alone or in combination with features of other stents of the invention and are conducive to percutaneous delivery thereof.

Methods for insertion of the replacement heart valves of the invention include delivery systems that can maintain the stent structures in their compressed state during their insertion and allow or cause the stent structures to expand once they are in their desired location. The methods may include implantation of the stent structures using either an antegrade or retrograde approach.

One embodiment of a stent of the invention comprises a tubular wire structure including multiple wires that extend generally in the direction of the longitudinal axis of the stent. A bioprosthesis can be attached to the wires of this stent in certain, predetermined locations and preferably will be sewn to the wires in such a way that the material from which the bioprosthesis is made will not be damaged during compression and/or expansion of the stent and attached bioprosthesis. In one embodiment, the stent includes three commissure attachment areas, where each of these areas is used as a connection location for one of the commissure extensions of a bioprosthesis.

The stented valves of the invention can use an external tubular material, such as a bovine jugular vain, pericardial tissue, PTFE graft material, polyester cloth, and other materials, to facilitate attachment of leaflets to the stent or tubular material. Attachment options can then be used that differ from using direct attachment of leaflets to the stent structure. In this way, the stent may not be as subject to long term fatigue of its valve leaflets because the loading forces on the leaflet attachment locations are transferred from a rigid stent structure to a flexible tubular structure.

BRIEF DESCRIPTION OF THE DRAWINGS

The present invention will be further explained with reference to the appended Figures, wherein like structure is referred to by like numerals throughout the several views, and wherein.

DETAILED DESCRIPTION

As referred to herein, the prosthetic heart valves used in accordance with the various devices and methods of heart valve delivery of the invention may include a wide variety of different configurations, such as a prosthetic heart valve having tissue leaflets or a synthetic heart valve having polymeric, metallic, or tissue-engineered leaflets, and can be specifically configured for replacing any heart valve. That is, while much of the description herein refers to replacement of aortic valves, the prosthetic heart valves of the invention can also generally be used for replacement of native mitral, pulmonic, or tricuspid valves, for use as a venous valve, or to replace a failed bioprosthesis, such as in the area of an aortic valve or mitral valve, for example.

In general, the stents described herein include a support structure comprising a number of strut or wire portions arranged relative to each other to provide a desired compressibility, strength, and leaflet attachment zone(s) to the heart valve. Other details on particular configurations of the stents of the invention are also described below; however, in general terms, stents of the invention are generally tubular support structures, and a bioprosthesis will be secured within the inner area of the tubular support structure to provide a valved stent.

In more general terms, the combination of a support structure with one or more leaflets of a bioprosthesis can assume a variety of other configurations that differ from those shown and described, including any known prosthetic heart valve design. In certain embodiments of the invention, the support structure with leaflets utilize certain features of known expandable prosthetic heart valve configurations, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "Percutaneous Insertion of the Pulmonary Valve", Pediatric Cardiology, 2002; 39:1664-1669; Anderson H R, et al., "Transluminal Implantation of Artificial Heart Valves", EUR Heart J., 1992; 13:704-708; Anderson, J. R., et al., "Transluminal Catheter Implantation of New Expandable Artificial Cardiac Valve", EUR Heart J., 1990, 11: (Suppl) 224a; Hilbert S. L., "Evaluation of Explanted Polyurethane Trileaflet Cardiac Valve Prosthesis", J Thorac Cardiovascular Surgery, 1989; 94:419-29; Block P C, "Clinical and Hemodynamic Follow-Up After Percutaneous Aortic Valvuloplasty in the Elderly", The American Journal of Cardiology, Vol. 62, Oct. 1, 1998; Boudjemline, Y., "Steps Toward Percutaneous Aortic Valve Replacement", Circulation, 2002; 105:775-558; Bonhoeffer, P., "Transcatheter Implantation of a Bovine Valve in Pulmonary Position, a Lamb Study", Circulation, 2000:102:813-816; Boudjemline, Y., "Percutaneous Implantation of a Valve in the Descending Aorta In Lambs", EUR Heart J, 2002; 23:1045-1049; Kulkinski, D., "Future Horizons in Surgical Aortic Valve Replacement: Lessons Learned During the Early Stages of Developing a Transluminal Implantation Technique", ASAIO J, 2004; 50:364-68; the teachings of which are all incorporated herein by reference).

Orientation and positioning of the valves of the invention in a patient may be accomplished either by self-orientation of the stents (such as by interference between features of the stent and a previously implanted stent or valve structure) or by manual orientation of the stent to align its features with anatomical features or features of a previously implanted bioprosthetic structure, such as can be accomplished using fluoroscopic visualization techniques, for example. For example, when aligning the stents of the invention with native anatomical structures, they should be aligned so as to not block the coronary arteries, and native mitral or tricuspid valves should be aligned relative to the anterior leaflet and/or the trigones/commissures to allow normal functioning of these structures.

Some embodiments of the support structures of the stents described herein can comprise a series of wires or wire segments arranged so that they are capable of transitioning from a collapsed state to an expanded state. In some embodiments, a number of individual wires comprising the support structure can be formed of a metal or other material. These wires are arranged in such a way allows for folding or compressing the support structure to a contracted state in which its internal diameter is greatly reduced from its internal diameter when it is in an expanded state. In its collapsed state, such a support structure with attached valves or leaflets can be mounted over a delivery device, such as a balloon catheter, for example. The support structure is configured so that it can be changed to its expanded state when desired, such as by the expansion of a balloon catheter. The delivery systems used for such a stent should be provided with degrees of rotational and axial orientation capabilities in order to properly position the stent at its desired location within the patient.

The wires of the support structure of the stents in other embodiments can alternatively be formed from a shape memory material such as a nickel titanium alloy (e.g., Nitinol). With this material, the support structure is self-expandable from a contracted state to an expanded state, such as by the application of heat, energy, and the like, or by the removal of external forces (e.g., compressive forces). This support structure can also be repeatedly compressed and re-expanded without damaging the structure of the stent. In addition, the support structure of such an embodiment may be laser cut from a single piece of material or may be assembled from a number of different components. For these types of stent structures, one example of a delivery system that can be used includes a catheter with a retractable sheath that covers the stent until it is to be deployed, at which point the sheath can be retracted to allow the stent to expand.

Figure 1:
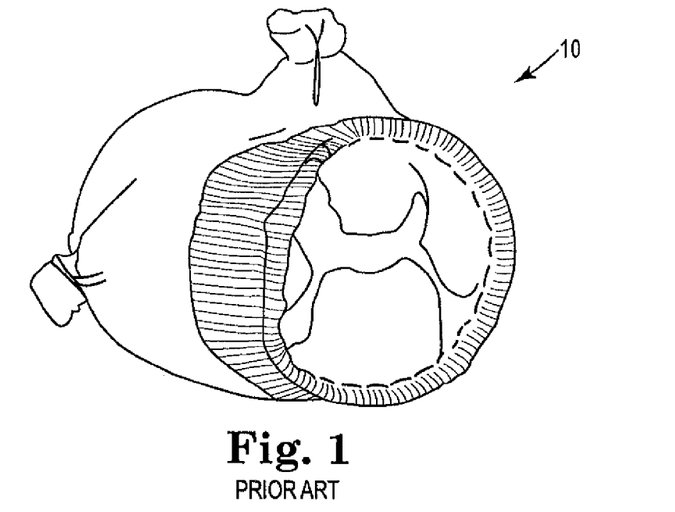
FIG. 1 is a perspective view of a prior art aortic root bioprosthesis.
Figure 2:
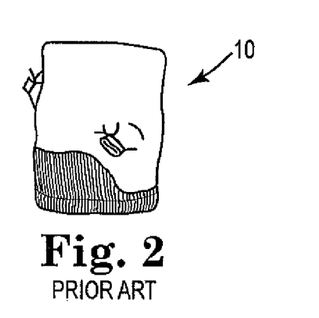
FIG. 2 is a front view of the bioprosthesis of FIG. 1.
Figure 3:
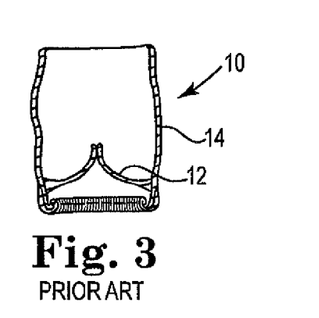
FIG. 3 is a cross-sectional view of the bioprosthesis of FIG. 2.

Referring now to the Figures, wherein the components are labeled with like numerals throughout the several Figures, and initially to FIGS. 1-7, multiple variations of a stentless bioprosthesis are illustrated. In particular, FIG. 1 illustrates an aortic root bioprosthesis 10, such as is commercially available from Medtronic, Inc. as the "Freestyle Bioprosthesis". Bioprosthesis 10 and other bioprostheses of this type are commonly referred to as stentless bioprostheses, which are designed to mimic the human physiology, create physiologic flow, and closely emulate the performance of the native aortic valve. As illustrated, bioprosthesis 10 includes an outer tubular shape having a covering material over a tube edge at one end that is provided to cover all exposed porcine myocardium. The covering material may be made of polyester, for example. The bioprosthesis 10, and other bioprostheses described herein, include one or more movable leaflets positioned within their internal tubular area. In many embodiments, the bioprostheses will have two or three leaflets; however it is possible that only one leaflet is provided and/or that the bioprosthesis includes more than three leaflets. FIGS. 2 and 3 are front and cross-sectional views, respectively, of the bioprosthesis 10. Bioprosthesis 10 includes an outer tubular portion 14 with an inner wall from which multiple leaflets 12 extend. This bioprosthesis 10 is used in surgical techniques for replacing the patient's entire native aortic root and valve.

Figure 4:
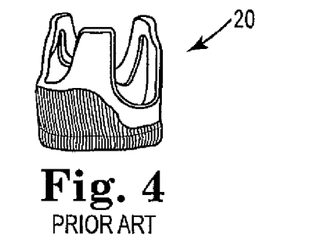
FIG. 4 is a front view of another embodiment of a prior art aortic root bioprosthesis.
Figure 5:
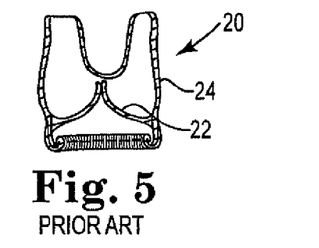
FIG. 5 is a cross-sectional view of the bioprosthesis of FIG. 4.

FIGS. 4 and 5 are front and cross-sectional views, respectively, of an alternative arrangement of a stentless bioprosthesis 20, where it is understood that different patient needs and surgeon preferences can be factored into selecting the most appropriate bioprosthesis for a particular patient. Bioprosthesis 20 includes an outer tubular portion 24 with an inner wall from which multiple leaflets 22 extend. Bioprosthesis 20 can be referred to as a "Prestyled Freestyle Complete Subcoronary Bioprosthesis" and is provided with scallops for the noncoronary sinus, the right coronary sinus, and the left coronary sinus.

Figure 6:
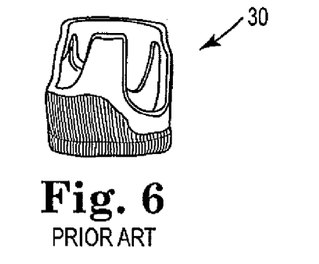
FIG. 6 is a front view of another embodiment of a prior art aortic root bioprosthesis.
Figure 7:
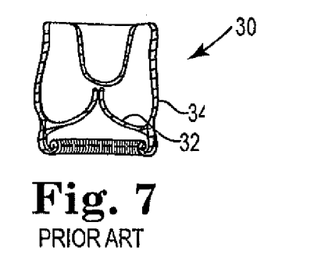
FIG. 7 is a cross-sectional view of the bioprosthesis of FIG. 6.

FIGS. 6 and 7 are front and cross-sectional views, respectively, of yet another alternative arrangement of a stentless bioprosthesis 30, which is referred to as a "Prestyled Freestyle Modified Subcoronary Bioprosthesis". Bioprosthesis 30 includes an outer tubular portion 34 with an inner wall from which multiple leaflets 32 extend. This bioprosthesis 30 includes scallops for only the right and left coronary sinuses. Any of these bioprostheses, which are typically implantable using standard surgical techniques, may be used with the techniques and systems described herein for implantation without the use of sutures.

Figure 8:
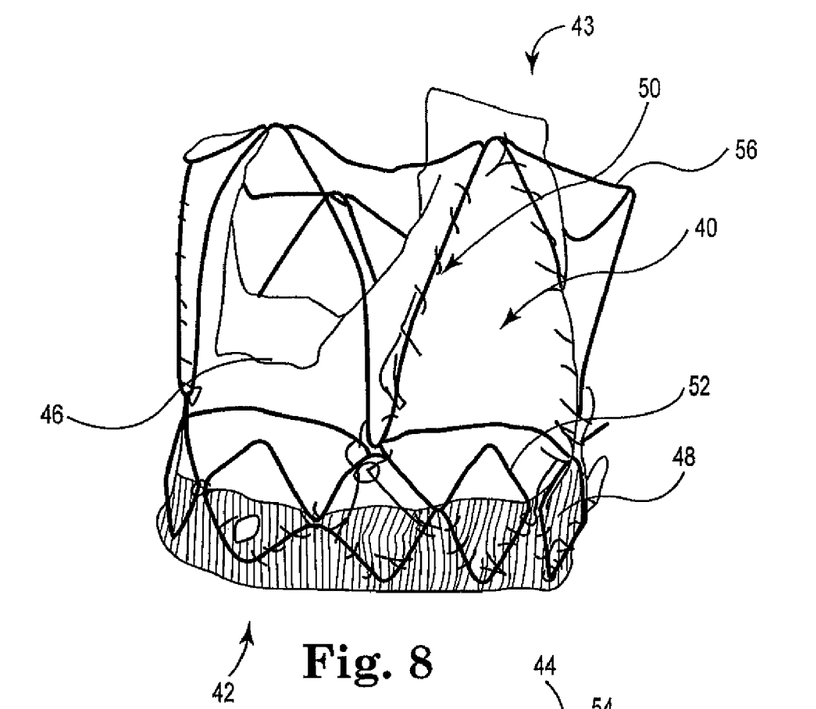
FIGS. 8 and 9 are front and perspective views, respectively, of another embodiment of a bioprosthesis attached to a stent, in accordance with the invention.
Figure 9:
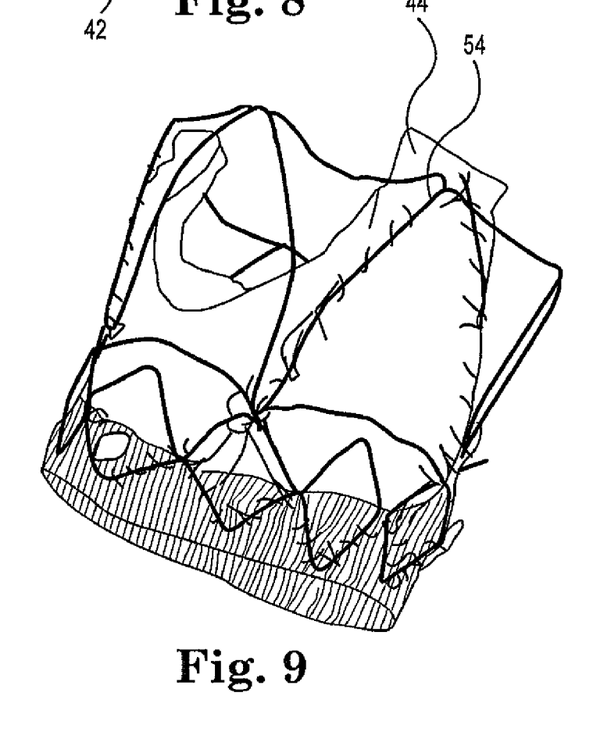

FIGS. 8 and 9 are front and perspective views, respectively, of a stentless bioprosthesis 40 positioned within a stent frame 50. The bioprosthesis 40 includes an inflow end 42, an outflow end 43, three commissure extensions 44, and a scallop or scalloped area 46 between adjacent pairs of extensions 44. Bioprosthesis 40 further includes material 48, such as a polyester cloth, that covers at least a portion of the inflow end 42 of the bioprosthesis. As shown, the material 48 is positioned between the outer surface of the bioprosthesis 40 and the inner surface of the wires that make up the stent 50. The material 48 then extends over the edge or end of the bioprosthesis 40 and into its interior tubular surface. The material 48 can extend along a desired distance of the wall of this interior tubular surface. Stent 50 comprises a series of wires arranged in a generally tubular shape, and specifically includes multiple diamond-shaped structures 52 extending around the perimeter at the inflow end 42. Stent 50 further includes plural U-shaped or V-shaped structures 54 that extend longitudinally along the length of the stent 50. The structures 54 each have an end that generally extends from the peaks of structures 52. Adjacent structures 54 can be connected to each other at or near their respective peaks by additional support wires 56.

In accordance with the invention, each of the commissure extensions 44 is attached to a V-shaped structure 54 with stitches that are spaced from each other and extend along the both sides and the peak of each structure 54. The stitching can be performed using standard suture material, which has a first end that can be terminated at one end of each structure 54 and a second end that can be terminated at the other end of the same structure 54, for example. Alternatively, a different stitching pattern can be used. The bioprosthesis 40 is additionally secured at its inflow end 42 to the stent frame 50 by suturing the covering material 48 and/or the tubing material to the diamond-shaped structures 52 in a zigzag pattern, as shown. While these figures only illustrate stitching along the lower portion or edge of each of the structures 52, the inflow end 42 could be additionally secured by stitching along the upper portion or edge of the structures 52. However, the stitching pattern illustrated in FIGS. 8 and 9 can be sufficient to provide support of the valve annulus, in certain applications.

Figure 10:
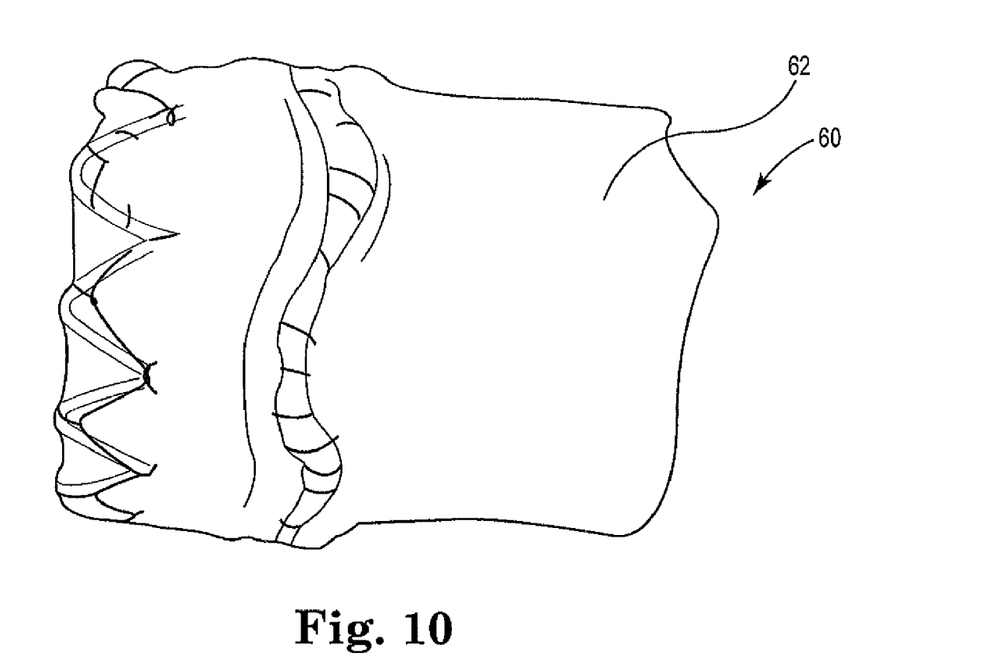
FIG. 10 is a side view of a stented valve with an outer tubing material layer.
Figure 11:
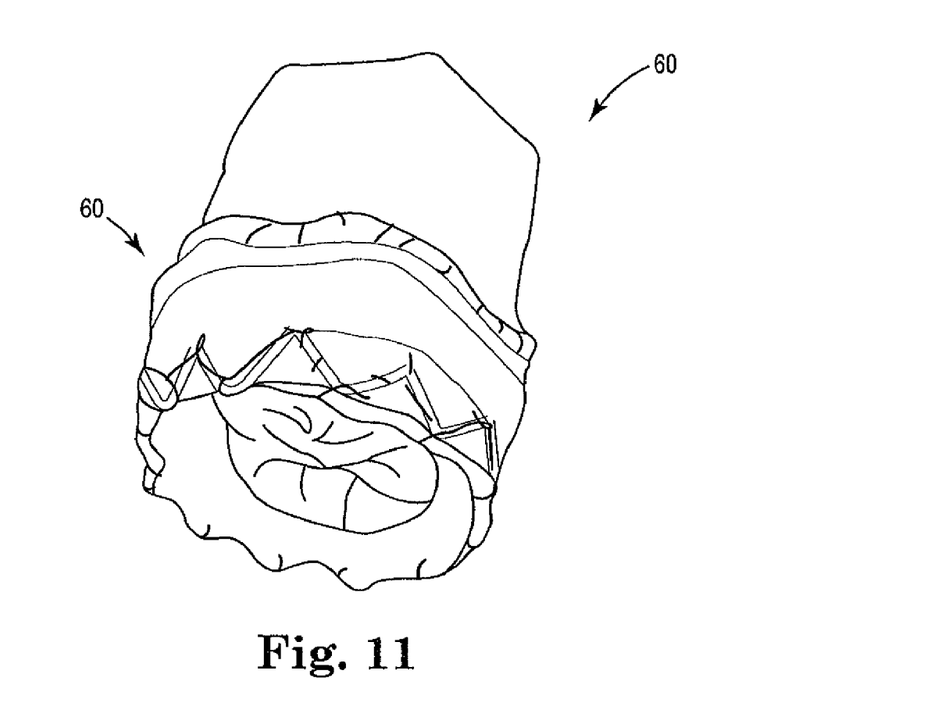
FIG. 11 is a perspective end view of the stented valve of FIG. 10.

FIGS. 10 and 11 are side and perspective views, respectively, of another stented valve 60 that can utilize the same or a different structure for its stent as the stent frame 50 discussed above relative to FIGS. 8 and 9. Alternatively, a different stent structure can be used. In any case, stented valve 60 includes a stent frame (not visible in these figures) surrounded by a tube material 62 that can comprise a bovine jugular vein, for example. That is, the tube material 62 is positioned on the outside of the stent frame. In such a case, porcine leaflets can be positioned within the inner area of the tube material 62. The tube material 62 can be attached to the stent frame by stitching along the lower portion of diamond-shaped structures of the stent frame and/or by stitching the components to each other in other locations. This attachment of the tube material to the stent instead of using direct attachment of leaflets, such as porcine leaflets, to the stent can transfer long-term structural fatigue due to physiologic pulsatile loading conditions from the porcine leaflets to the tube/stent structure. This can potentially increase the functional life of the tissue valve leaflets.

Figure 12:
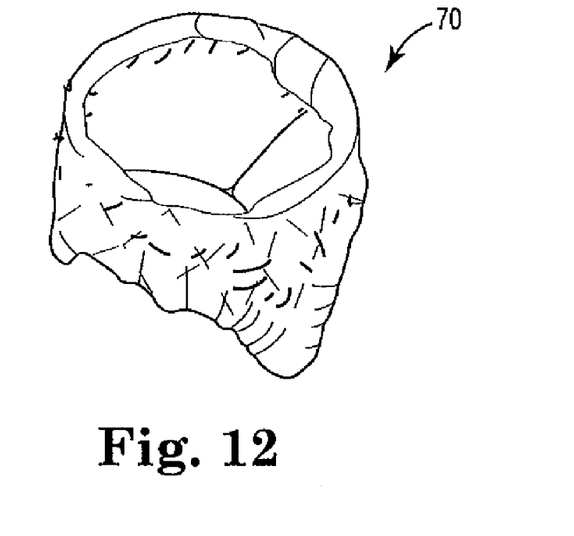
FIG. 12 is another perspective view of an expandable stent having a covering of tissue.

FIG. 12 illustrates another embodiment of an expandable stented valve 70, which includes a stent that is covered with bovine jugular vein tissue. Porcine tissue is attached within the vein tissue to protect the leaflets from making direct contact with the wire stent frame. As shown, the tissue is attached to the stent via stitching along portions of the stent frame. Different stitching configurations can alternatively be used.

Figure 13:
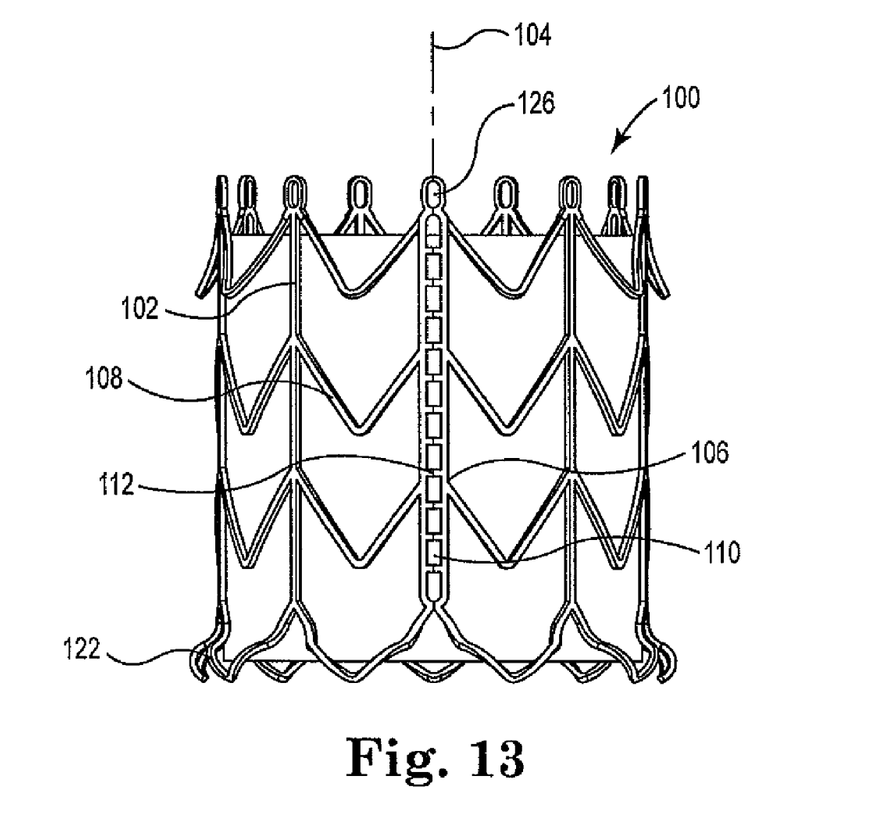
FIG. 13 is a front view of an exemplary stent frame positioned over a mandrel.

FIG. 13 illustrates another exemplary stent frame 100 to which a stentless bioprosthesis can be attached, such as any of the bioprostheses illustrated in FIGS. 1-7. The stent is shown on a mandrel so that the front wires can be viewed more clearly. The stent 100 may be made of a self-expanding material, such as Nitinol, for example, or may be configured so that it is expandable with the application of force provided by an expanding balloon. This stent 100 may be sized to be short enough that it can be referred to as a sub-coronary stent (e.g., 25 mm long) to enable stent placement below the coronary arteries in the aorta.

In one embodiment, the stent 100 is generally tubular in shape and includes multiple longitudinal or vertical wires 102 that extend generally parallel to a longitudinal axis 104 of the stent. The wires 102 are spaced from each other around the periphery of the generally tubular shape of the stent 100. Stent 100 further includes features to which tissue can be attached to make the stent into a valve, such as commissure attachment posts 106. Commissure attachment posts 106 can each include two longitudinal wires that are spaced closer to each other than the spacing of the wires 102 from each other.

In this embodiment, stent 100 includes three commissure attachment posts 106, where each of the posts 106 can be used as a connection location for one of the commissure extensions of a bioprosthesis, such as extensions 44 of bioprosthesis 40. Alternatively, more or less than three posts 106 can be provided for a valve having more or less than three leaflets, respectively. In addition to providing the structure for attachment of commissures, the posts 106 also provide additional stability to the stent 100. Stent 100 further includes multiple V-shaped wire structures 108 between pairs of wires 102 and/or between a wire 102 and an adjacent attachment post 106. Although the stent 100 is shown as having three of these V-shaped wires 108 spaced longitudinally from each other between adjacent vertical wire structures, there instead may be more or less than three V-shaped wires. All or some of the wires 108 can be flared at least slightly outward relative to the outer tubular shape of the stent 100, thereby creating integrated flange structures that can be used to capture the native leaflets when the stent is implanted in a patient.

Additional wire structures 122 are positioned at an end 120 of the stent 100, which are generally V-shaped, with the peak of each of the "V" structures oriented in generally the same direction as the peaks of the wires 108. All or some of these wire structures 122 are also flared at least slightly outward relative to the outer tubular shape of the stent 100. The amount and angle at which the various wire structures extend relative to the tubular outer shape of the stent can be selected for capturing native patient anatomical features. In addition, the flare of the wire structures 122 can help to prevent or minimize leakage between the implant and the native annulus and/or to provide a physical and/or visual docking feature to secure the stent 100 against a wall of an opening in the heart to prevent migration of the stent, for example.

One end of all or some of the wires 102 and posts 106 can further include a loop or eyelet 126 that can be used for attachment to a delivery system and/or tissue valve, for example. The single-sided eyelet attachment end can be used in a resheathable delivery system for both antegrade and retrograde procedures, for example.

This embodiment of a stent includes spaces or openings 110 that are created by the use of horizontal members 112 between the two wires that make up the attachment posts 106. These openings 110 provide locations through which suture material, needles, and/or other fastening materials can be inserted for attachment of the bioprosthesis to the stent frame. In addition, the horizontal members 112 can be used as defined anchoring points for the fastening materials. For example, a suture material can be inserted through a first opening 110 and then through another opening 110 in a predetermined pattern to stitch valve material to the commissure extensions of the bioprosthesis. The horizontal members 112 can further be used as anchoring structures that limit vertical movement of sutures or other attachment mechanisms. In order to attach other areas of the bioprosthesis to the stent 100, the scalloped areas, such as those described above relative to bioprosthesis 40, can be stitched along selected wires of the stent 100, such as along certain shaped wires 108 and/or vertical wires 102, for example.

A number of systems, components, and devices are described below for attachment of valve material (e.g., tissue leaflets) within the interior area of a stent structure. It is understood that the systems that are shown and described herein for this purpose can be used with stent configurations described above and/or other stent constructions.

Figure 18:
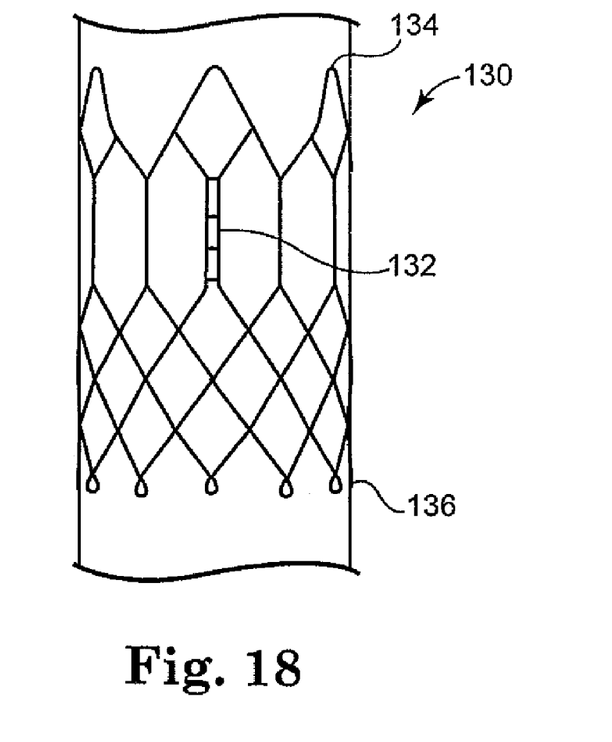
FIG. 18 is a front view of an exemplary stent frame positioned over a mandrel.

FIG. 18 illustrates another exemplary stent frame 130 to which a stentless bioprosthesis can be attached, such as any of the bioprotheses illustrated in FIG. 1-7. This tent frame 130 is shown on a mandrel so that the front wires can be viewed more clearly. The stent 130 may be sized to be tall or long enough that it can be referred to as a supra-coronary stent in that it can be placed to extend above the coronary arteries in the aorta. Stent 130 includes at least one longitudinal post 132 that extends generally along the annular region of the stent 130 and has a height that accommodates attachment of leaflet material. With this stent 130, wire structure extends between one end of the post 132 and a first end 134 of the stent (which may be referred to as the aortic aspect of the stent), and additional wire structure extends between the other end of the post 132 and a second end 136 of the stent (which may be referred to as the ventricular aspect of the stent). The stent 130 may include one longitudinal post 132 for each commissure extension of the bioprosthesis to which the stent 130 is attached, if desired. That is, for a three-leaflet bioprosthesis, three posts 132 can be provided.

Figure 19:
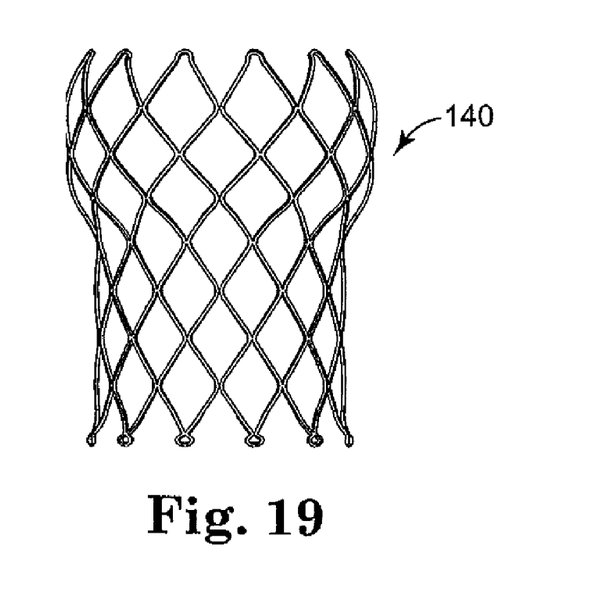
FIG. 19 is a front view of another exemplary stent frame that can be used with a valve in accordance with the invention.

FIG. 19 illustrates another exemplary stent frame 140 to which a stentless bioprosthesis can be attached, such as any of the bioprostheses illustrated in FIGS. 1-7. Stent 140 includes a wire structure arranged as a generally regular diagonal criss-cross pattern along its length. The stent 140 further includes a bulbous shape to the wires at one end. The commissure extensions of the bioprosthesis can be attached to particular wires of the stent 140 to securely attach the components to each other.

Figure 14:
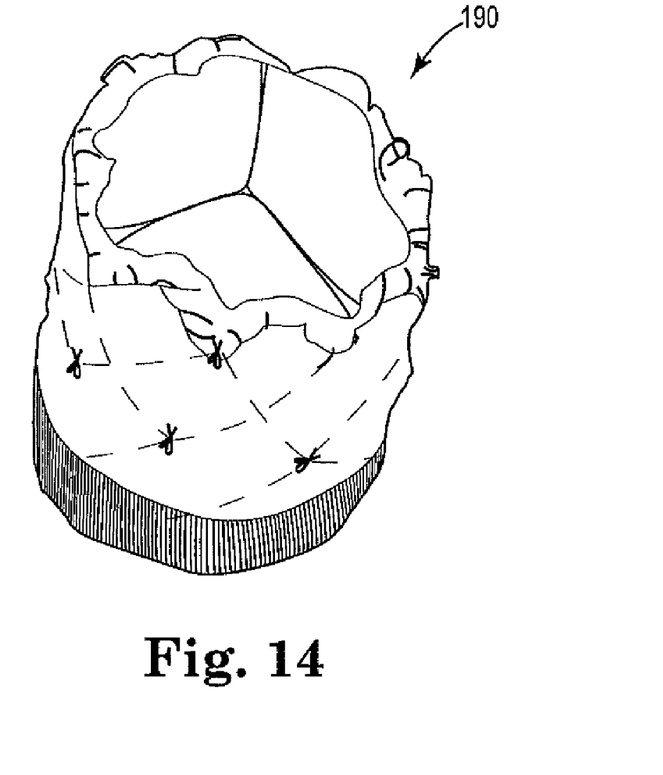
FIG. 14 is a top perspective view of an embodiment of a stented valve.
Figure 15:
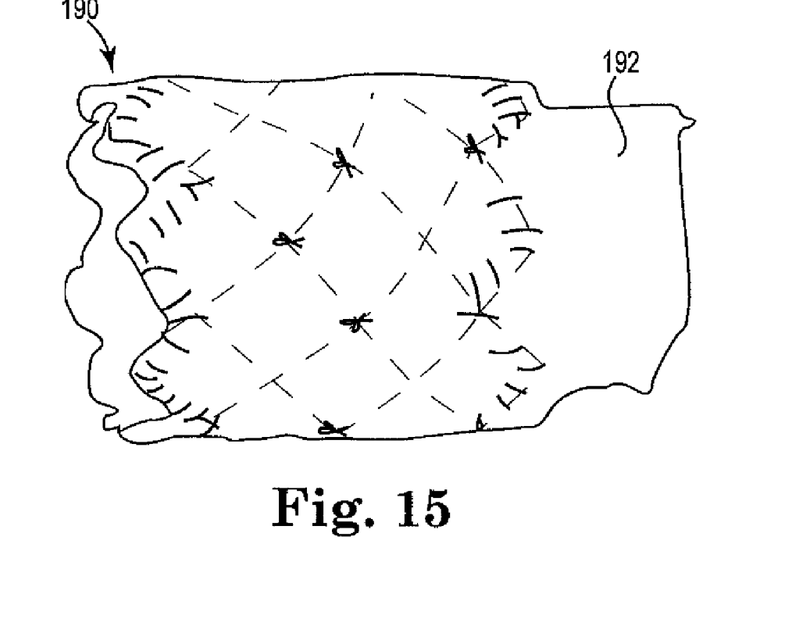
FIG. 15 is a side view of the stented valve of FIG. 14.

FIGS. 14 and 15 illustrate another embodiment of a valve 190 made with a bovine jugular vein or tube cover, as discussed above relative to FIGS. 10 and 11. The tubular tissue cover includes a tubular tissue extension 192 at one end to provide an additional anchoring feature to guard against migration for a surgical sutureless implant. The tissue extension 192 is positioned on the outflow side of the stent and can be incorporated into an aortotomy closure for aortic valve replacement. It can alternatively be used for pulmonary artery and/or right ventricular outflow tract reconstruction for pulmonary valve replacement procedures. In order to use the valve 190 for aortic valve replacement, windows would need to be cut into the tube in the sinus areas of the stent to allow for unobstructed coronary flow. In this embodiment, the tube cover (e.g., bovine jugular vein section) is placed over the outer surface of the stent, and then the valve is placed in the interior area of the stent. A single suture line secures both the proximal end of the valve and the bovine jugular vein to proximal crowns of the stent. Valve commissures and the distal bovine tube are secured to the stent cells with interrupted anti-hammocking stitches, for example, at locations as required to secure the tissue and maintain leaflet coaptation.

It is noted that in many of the stent embodiments shown and described herein, the aspect ratio of certain portions of the stent can be somewhat different from that shown. Further, stent embodiments described herein may be modified to include additional structure for attachment of tissue for the valve, such as the vertical stent posts described in many of the embodiments.

Figure 16:
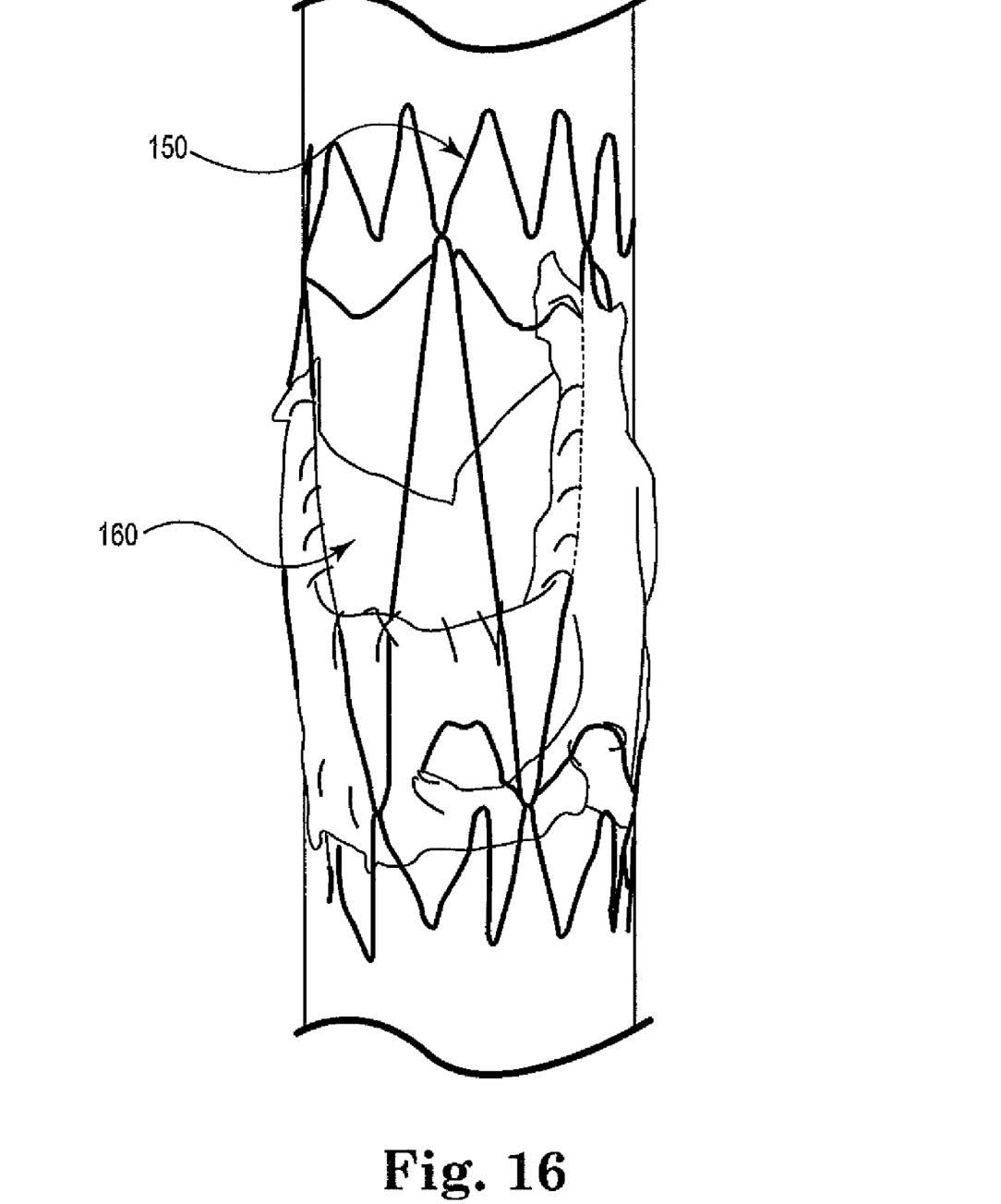
FIG. 16 is a side view of a portion of a delivery system positioned relative to a stent and attached bioprosthesis, where the stent is in a partially compressed condition.
Figure 17:
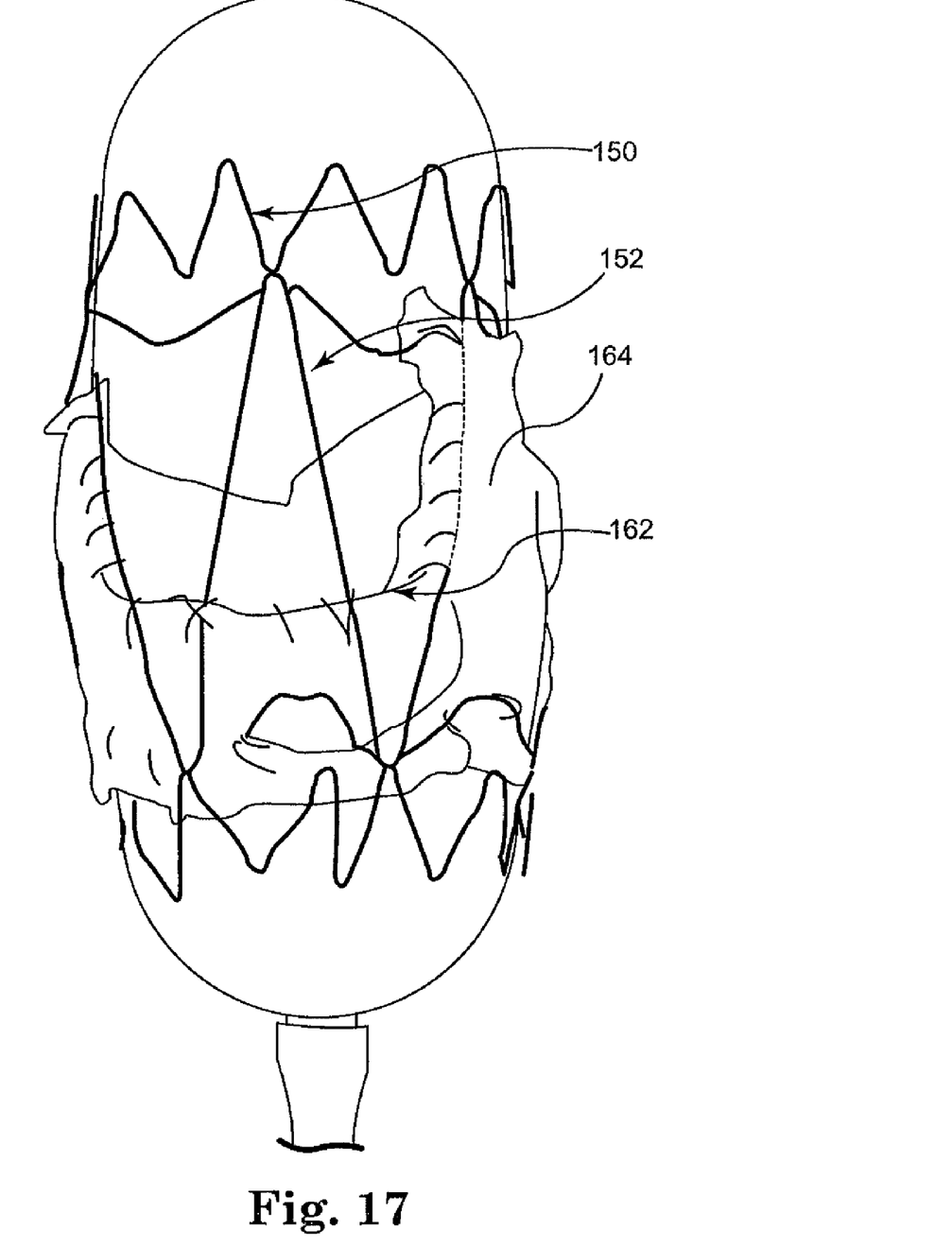
FIG. 17 is a side view of the delivery system and stented bioprosthesis of FIG. 16, where the stent is in a partially expanded condition.

FIGS. 16 and 17 illustrate a stent to which a bioprosthesis is attached for implantation using transcatheter delivery methods. In particular, FIG. 16 shows a stent 150 and an attached bioprosthesis 160, each of which is in its at least partially compressed configuration. FIG. 17 shows the stent 150 and bioprosthesis 160 at least partially expanded by a balloon-type delivery system. In the illustrated embodiment, the bioprosthesis 160 includes scalloped openings or areas 162 that can be positioned to allow fluid communication between the bioprosthesis and the coronary arteries. The scalloped openings 162 are each positioned between commissure extensions 164 of the bioprosthesis.

Points along the edge of each scalloped opening 162 of the bioprosthesis 160 are attached to certain, predetermined wires of the stent 150. In the illustrated embodiment, the stent 150 includes a number of wires arranged into relatively narrow V-shaped structures 152 that extend longitudinally relative to a central axis of the stent 150. In this embodiment, the stent 150 is provided with one V-shaped structure 152 to correspond with each commissure extension 164, and one V-shaped structure 152 to correspond with each of the areas between the extensions 164 (e.g., scalloped areas 162). The stitching pattern used to attach the bioprosthesis to the stent includes providing stitches that can slide along the V-shaped structures to allow for movement of the components relative to each other during the compression and expansion of the bioprosthesis and to allow for the necessary dimensional changes of the stent and its attached bioprosthesis. This movement of the stitches along the stent wires will prevent or minimize stresses that might otherwise be placed on stitches having a smaller available range of motion when the components are being reconfigured during compression and/or expansion of the device.

Delivering any balloon-expandable stents of the invention to the implantation location can be performed percutaneously. In general terms, this includes providing a transcatheter assembly, including a delivery catheter, a balloon catheter, and a guide wire. Some delivery catheters of this type are known in the art, and define a lumen within which the balloon catheter is received. The balloon catheter, in turn, defines a lumen within which the guide wire is slideably disposed. Further, the balloon catheter includes a balloon that is fluidly connected to an inflation source. It is noted that if the stent being implanted is a self-expanding type of stent, the balloon would not be needed and a sheath or other restraining means would be used for maintaining the stent in its compressed state until deployment of the stent, as described herein. In any case, for a balloon-expandable stent, such as stent 150 of FIGS. 16 and 17, the transcatheter assembly is appropriately sized for a desired percutaneous approach to the implantation location. For example, the transcatheter assembly can be sized for delivery to the heart valve via an opening at a carotid artery, a jugular vein, a sub-clavian vein, femoral artery or vein, or the like. Essentially, any percutaneous intercostals penetration can be made to facilitate use of the transcatheter assembly.

Prior to delivery, the stent is mounted over the balloon in a contracted state to be as small as possible without causing permanent deformation of the stent structure. As compared to the expanded state, the support structure is compressed onto itself and the balloon, thus defining a decreased inner diameter as compared to an inner diameter in the expanded state. While this description is related to the delivery of a balloon-expandable stent, the same basic procedures can also be applicable to a self-expanding stent, where the delivery system would not necessarily include a balloon and expansion thereof, but would preferably include the use of a sheath or some other type of configuration for maintaining the stent in a compressed condition until it is released for deployment.

With the stent mounted to the balloon, the transcatheter assembly is delivered through a percutaneous opening (not shown) in the patient via the delivery catheter. The implantation location is located by inserting the guide wire into the patient, which guide wire extends from a distal end of the delivery catheter, with the balloon catheter otherwise retracted within the delivery catheter. The balloon catheter is then advanced distally from the delivery catheter along the guide wire, with the balloon and stent positioned relative to the implantation location. In an alternative embodiment, the stent is delivered to an implantation location via a minimally invasive surgical incision (i.e., non-percutaneously). In another alternative embodiment, the stent is delivered via open heart/chest surgery. In one embodiment of the stents of the invention, the stent includes a radiopaque, echogenic, or MRI visible material to facilitate visual confirmation of proper placement of the stent. Alternatively, other known surgical visual aids can be incorporated into the stent. The techniques described relative to placement of the stent within the heart can be used both to monitor and correct the placement of the stent in a longitudinal direction relative to the length of the anatomical structure in which it is positioned.

Once the stent is properly positioned, the balloon catheter is operated to inflate the balloon, thus transitioning the stent to an expanded state. Alternatively, where the support structure is formed of a shape memory material, the stent can be allowed to expand to its expanded state by removal of the external forces (e.g., a sheath).

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A stented valve comprising:
    a compressible and expandable stent structure comprising:
        a generally tubular body portion having an interior area;
        a longitudinal axis; and
        at least two v-shaped commissure structures, each of which comprises a first commissure segment having a first end and a second end, and a second commissure segment having a first end and a second end, wherein the first and second commissure segments intersect at their second ends at an intersection point; and
    a bioprosthetic valve positioned at least partially within the interior area of the tubular body portion of the stent structure and comprising:
        an outer tubular portion comprising at least two commissure extensions and an inner wall from which a plurality of leaflets extend; and
        at least one scalloped portion extending between adjacent commissure extensions;
    wherein each commissure extension is directly secured to one of the v-shaped commissure structures with a plurality of suture loops extending along a length between the first and second ends of each of the first and second commissure segments, wherein each plurality of suture loops is slideable along one of the first and second commissure segments between its first and second ends to allow for free movement of each of the commissure extensions relative to the commissure segments of the stent structure along its longitudinal axis during compression and expansion of the stent structure.

2. The stented valve of claim 1, wherein each of the at least one scalloped portions is secured to the stent structure.

3. The stented valve of claim 2, wherein the scalloped portions are sutured to the stent structure so that they are slideable relative to the stent structure.

4. The stented valve of claim 1, wherein the stent structure is self-expandable from a compressed condition to an expanded condition with the removal of an external compressive force.

5. The stented valve of claim 1, wherein the stent structure is expandable from a compressed condition to an expanded condition with the application of an outward expansion force.

6. The stented valve of claim 1, wherein the outer tubular portion of the bioprosthetic valve comprises three commissure extensions.

7. The stented valve of claim 6, wherein the bioprosthetic valve comprises three leaflets.

8. The stented valve of claim 1, wherein the first end of each of the first and second commissure segments of each of the v-shaped commissure structures is positioned between an inflow end of the stent structure and a bottom edge of one of the scalloped portions.

9. The stented valve of claim 8, wherein the intersection point of each of the v-shaped commissure structures is positioned between the bottom edge of one of the scalloped portions and an outflow end of the stent structure.

10. The stented valve of claim 1, further comprising a support wire extending between the intersection points of two adjacent v-shaped commissure structures.

* * * * *